United States Patent [19]

Orlek et al.

[11] Patent Number: 5,362,739
[45] Date of Patent: Nov. 8, 1994

[54] AZABICYCLIC COMPOUNDS AND PHARMACEUTICAL COMPOSITIONS CONTAINING THEM

[75] Inventors: Barry S. Orlek; Steven M. Bromidge, both of Harlow, England, Richard E. Faulkner, deceased, late of Harlow, England, by Geoffrey E. Faulkner, executor

[73] Assignee: Beecham Group p.l.c., England

[21] Appl. No.: 975,555

[22] PCT Filed: Aug. 22, 1991

[86] PCT No.: PCT/GB91/01424

§ 371 Date: Mar. 19, 1993

§ 102(e) Date: Mar. 19, 1993

[87] PCT Pub. No.: WO92/03435

PCT Pub. Date: Mar. 5, 1992

[30] Foreign Application Priority Data

Aug. 24, 1990 [GB] United Kingdom ............... 9018675
May 11, 1991 [GB] United Kingdom ............... 9110255

[51] Int. Cl.⁵ .................. A61K 31/435; C07D 471/08
[52] U.S. Cl. ..................................... 514/299; 546/112
[58] Field of Search ......................... 546/112; 514/299

[56] References Cited

U.S. PATENT DOCUMENTS

| | | | |
|---|---|---|---|
| 4,710,508 | 12/1987 | Bergmeier et al. | 514/357 |
| 4,786,648 | 11/1988 | Bergmeier et al. | 514/357 |
| 4,798,841 | 1/1989 | Downs et al. | 514/357 |
| 4,927,837 | 5/1990 | Galliani et al. | 514/331 |
| 4,937,239 | 6/1990 | Lauffer et al. | 514/183 |
| 5,015,655 | 5/1991 | Galliani et al. | 514/413 |
| 5,110,828 | 5/1992 | Bromidge et al. | 514/413 |

FOREIGN PATENT DOCUMENTS

| | | |
|---|---|---|
| 0094742 | 11/1983 | European Pat. Off. |
| 0239445 | 9/1987 | European Pat. Off. |
| 0257741 | 3/1988 | European Pat. Off. |
| 0261763 | 3/1988 | European Pat. Off. |
| 0271798 | 6/1988 | European Pat. Off. |
| 0287356 | 10/1988 | European Pat. Off. |
| 0288394 | 10/1988 | European Pat. Off. |
| 0291673 | 11/1988 | European Pat. Off. |
| 0308283 | 3/1989 | European Pat. Off. |
| 0308284 | 3/1989 | European Pat. Off. |
| 0316718 | 5/1989 | European Pat. Off. |
| 0338723 | 10/1989 | European Pat. Off. |
| 0366561 | 5/1990 | European Pat. Off. |
| 0392803 | 10/1990 | European Pat. Off. |

Primary Examiner—Bernard Dentz
Attorney, Agent, or Firm—Linda E. Hall; Stuart R. Suter; Edward T. Lentz

[57] ABSTRACT

Compounds of the formula I

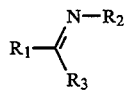

(I)

wherein $R_1$ represents

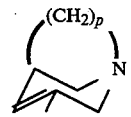

and the remainder of the variables are defined in the specification are useful in the treatment and/or prophylaxis of dementia in mammals.

7 Claims, No Drawings

AZABICYCLIC COMPOUNDS AND PHARMACEUTICAL COMPOSITIONS CONTAINING THEM

This invention relates to compounds having pharmaceutical activity, to a process for their preparation and their use as pharmaceuticals.

EP-0338723 and EP-0392803 (published 17 Oct. 1990) disclose certain azabicyclic compounds which enhance acetylcholine function via an action at muscarinic receptors.

A novel group of compounds has now been discovered which also enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

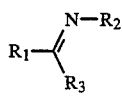
(I)

wherein $R_1$ represents

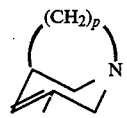

in which p represents 2 or 3;

$R_2$ is a group $OR_4$, where $R_4$ is $C_{1-4}$ alkyl, $C_{2-4}$ alkenyl, $C_{2-4}$ alkynyl, a group $OCOR_5$ where $R_5$ is hydrogen or $R_4$, or a group $NHR_6$ or $NR_7R_8$ where $R_6$, $R_7$ and $R_8$ are independently $C_{1-2}$ alkyl; and $R_3$ is hydrogen, chloro, fluoro, bromo, cyclopropyl, $C_{1-4}$ alkyl, $C_{1-3}$ alkyl substituted by one, two or three halogen atoms, or $R_3$ is a group $(CH_2)_nR_9$ where $R_9$ is —CN, —OH, —OCH$_3$, —SH, —SCH$_3$, —C≡CH or —CH=CH$_2$ and n is 0 or 1, with the proviso that when n is 0, $R_9$ is not —OH or —SH, or, when, $R_2$ is $OCOR_5$ or $NHR_6$, $R_3$ may not be hydrogen.

The term halogen includes bromine, chlorine, fluorine and iodine, preferably fluorine.

Compounds of formula (I) are capable of existing in a number of stereoisomeric forms including geometric isomers such as syn and anti and enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

The term pharmaceutically acceptable salt encompasses solvates and hydrates. Thus where compounds of formula (I) or pharmaceutically acceptable salts thereof form solvates or hydrates, these also form an aspect of the invention.

Preferably, p represents 2.

The groups $R_4$ and $R_5$ in $R_2$ are preferably selected from methyl, ethyl, allyl and propargyl. $R_6$, $R_7$ and $R_8$ are preferably methyl. Suitable values for $R_2$ include methoxy, ethoxy, allyloxy, propargyloxy, acetoxy and dimethylamino, preferably methoxy.

Suitable examples for $R_3$ include hydrogen, methyl, cyclopropyl, chloro, fluoro and bromo and when $R_3$ is a group $(CH_2)_nR_9$ and n is 0, suitable examples of $R_9$ include —CN, —OCH$_3$ or —C≡CH. When n is 1, an example of $R_9$ is CN.

The invention also provides a process for the preparation of a compound of formula (I), or a pharmaceutically acceptable salt thereof, which process comprises:

(a) reacting a compound of formula (II):

(II)

with a compound of formula (III):

(III)

wherein $R_1'$ represents $R_1$ or a group convertible thereto, $R_2'$ represents $R_2$ or hydroxy, and $R_3'$ represents $R_3$ or a group convertible thereto, converting $R_2'$ to $R_2$ when hydroxy, converting $R_1'$ and $R_3'$ when other than $R_1$ and $R_3$ to $R_1$ and $R_3$, wherein $R_1$, $R_2$ and $R_3$ are as defined in formula (I), and thereafter optionally forming a pharmaceutically acceptable salt;

(b) reacting a compound of formula (IV):

(IV)

with a compound of formula (V):

(V)

capable of generating an $R_3'$ nucleophile wherein $R_1'$ represents $R_1$ or a group convertible thereto, $R_3'$ represents $R_3$ or a group convertible thereto, converting $R_1'$ and $R_3'$ when other than $R_1$ and $R_3$ to $R_1$ and $R_3$, wherein $R_1$, $R_2$ and $R_3$ are as defined in formula (I), and thereafter optionally forming a pharmaceutically acceptable salt;

(c) reacting a compound of formula (IVa)

(IVa)

wherein $R_1'$ and $R_2$ are as defined in formula (IV), with a chlorinating, brominating or fluorinating agent, converting $R_1'$ when other than $R_1$ to $R_1$, optionally converting $R_3$ when chloro or bromo to other $R_3$ wherein $R_3$ is as defined in formula (I), and thereafter optionally forming a pharmaceutically acceptable salt;

(d) the nitrosation of a compound of formula (IVb) or (IVc):

(IVb)

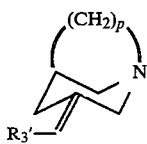
(IVc)

wherein $R_1'$ and $R_3'$ are as defined in formula (II) and p is as defined in formula (I), and thereafter converting the resulting =NOH group to =NR$_2$ wherein R$_2$ is as defined in formula (I), converting $R_1'$ and $R_3'$ when other than $R_1$ and $R_3$ to $R_1$ and $R_3$ and thereafter optionally forming a pharmaceutically acceptable salt; or (e) reacting a compound of formula (IVd)

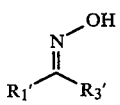
(IVd)

wherein $R_1'$ and $R_3'$ represent $R_1$ and $R_3$ as defined in formula (I) or groups convertible thereto, to convert the hydroxy group to R$_2$ as defined in formula (I), and thereafter converting $R_1'$ and $R_3'$ when other than $R_1$ and $R_3$ to $R_1$ and $R_3$ and optionally forming a pharmaceutically acceptable salt.

It will be appreciated that compounds of formula (IV) are identical to compounds of formula (I) in which $R_1'$ is $R_1$ and $R_3$ is chloro or bromo, and as such are themselves part of the invention.

The reaction between the compounds of formulae (II) and (III) is preferably carried out in a hydroxylic solvent such as methanol or ethanol, at ambient temperature, or where appropriate, at elevated temperature.

Where R$_2$ in compounds of formula (I) is a group OR$_4$, NHR$_6$ or NR$_7$R$_8$, a compound of formula (II) is conveniently reacted with a compound of formula (III) in which $R_2'$ is R$_2$.

Where R$_2$ in compounds of formula (I) is a group OCOR$_5$, a compound of formula (II) may be reacted with the compound of formula (III) in which $R_2'$ is hydroxy, with subsequent acylation of the resulting oxime of formula (IVd) by treatment with a suitable acylating agent such as an acyl halide, for example acetyl chloride.

The reaction between compounds of formulae (IV) and (V) may be carried out under standard conditions for the displacement of halogen by a nucleophile.

Where R$_3$ in compounds of formula (I) is fluoro, the residue M is suitably caesium, the caesium fluoride reagent being supported on calcium fluoride in dimethylformamide at elevated temperature for a prolonged period.

The nitrosation of the compound of formula (IVb) or (IVc) is preferably carried out using t-butyl nitrite and a base such as sodium ethoxide or, more preferably, potassium t-butoxide, and $R_3'$ is preferably an electron withdrawing group other than halo, such as CN.

The resulting =NOH group in the oxime of formula (IVd) may be converted to =NR$_2$ by conventional routes such as acylation as described above or alkylation with an alkylating agent such as methyltosylate or an alkyl halide for example methyl iodide. It will be appreciated that $R_3'$ is preferably other than halo, such as CN.

The product of the reaction of compounds of formulae (II) and (III) and formulae (IV) and (V) and the nitrosation of the compound of formula (IVb) or (IVc) is a compound of formula (IIa):

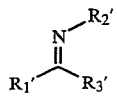
(IIa)

wherein $R_2'$ represents R$_2$ or hydroxy and $R_1'$ and $R_3'$ represent R$_1$ and R$_3$ or groups convertible thereto, and R$_1$, R$_2$ and R$_3$ are as defined in formula (I).

Intermediates of formula (IIa) wherein $R_1'$ is not R$_1$ when $R_2'$ and $R_3'$ are R$_2$ and R$_3$, also form part of the invention.

It will be appreciated that the reaction of compounds of formula (IVa) with a chlorinating, brominating or fluorinating agent will yield compounds of formula (I) wherein R$_3$ is chloro, bromo or fluoro. Suitable chlorinating agents include phosphorus pentachloride which undergoes reaction in nitromethane at reduced temperature, for example 0° C., and dichlorotriphenylphosphine or carbon tetrachloride/triphenyl phosphine which undergoes reaction in acetonitrile at elevated temperature, for example at the boiling point of the solvent. Suitable brominating agents include dibromotriphenylphosphine or carbon tetrabromide/triphenylphosphine which undergoes reaction in acetonitrile at elevated temperature, for example at the boiling point of the solvent. Suitable fluorinating agents include diethylaminosulphur trifluoride (DAST) which also undergoes reaction in acetonitrile at elevated temperature.

Conversion of the resulting R$_3$ halogen group when chloro or bromo to other R$_3$ groups may be effected by reaction variant (b) above.

Compounds of formula (II) and compounds of formulae (IV) and (IVa) may be prepared from an intermediate compound of formula (VI):

(VI)

in which L is a leaving group such as chloro, bromo, C$_{1-4}$ alkoxy or N-methoxy-N-methylamino and $R_1'$ is as defined in formula (II). A compound of formula (VI) in which L is preferably chloro or bromo may be reacted with N,O-dimethylhydroxylamine and the resulting N-methoxy-N-methylcarboxamide derivative reacted with a compound of formula (V), suitably disobutylaluminium hydride or lithium aluminium hydride or an organolithium such as methyl lithium or a Grignard reagent, to provide a compound of formula (II). Where R$_3$ is ethynyl, it is preferably protected in the compound of formula (V) which is suitably lithium (trimethylsilyl) acetylene. The trimethylsilyl protecting group is preferably removed after reaction of the compounds of formulae (II) and (III) by treatment with aqueous sodium hydroxide.

Where R$_3$ is cyclopropyl, a compound of formula (VI) in which L is preferably chloro or bromo may be treated with cyclopropyltrimethylsilane in the presence of aluminium trichloride in dichloromethane.

Where R$_3$ is CH$_2$CN, a compound of formula (VI) in which L is preferably C$_{1-4}$ alkoxy or N-methoxy-N-methylamino may be treated with a suitable organolithium or Grignard reagent, for example the reaction product of acetonitrile and lithium diisopropylamide. It will be appreciated that the resulting compound of formula (II) will be in the form of the lithium enolate salt.

A compound of formula (VI) may alternatively be reacted with a compound of formula (III) wherein $R_2'$ is $OR_4$, in chloroform or acetonitrile or a mixture as solvent, in the presence of a base such as pyridine or triethylamine, and the resulting derivative of formula (IVa) treated with a chlorinating or brominating agent to provide a compound of formula (IV) in which $R_2$ is $OR_4$.

Novel compounds of formulae (II), (IV), (IVa), (IVb), (IVc), (IVd) and (VI) also form part of the invention.

In particular, the invention provides intermediates of formula (XIII):

$$R_1'—Q \qquad (XIII)$$

wherein $R_1'$ is $R_1$ or a group convertible thereto and Q is selected from —$COR_3'$, —$CONHR_2$, —$CON(CH_3)OCH_3$, —$C(R_3')$=$NR_2'$ and —$CH_2$—$R_3'$, and $R_1'$ and $R_3'$ are $R_1$ and $R_3$ or groups convertible thereto and $R_2'$ is $R_2$ or hydroxy, provided that $R_1'$ is not $R_1$ when Q is —$C(R_3')$=$NR_2'$ and $R_2'$ and $R_3'$ are $R_2$ and $R_3$, including salts thereof.

Compounds of formula (VI) and (IVb) and certain compounds of formula (II) may conveniently be prepared by cyclising a compound of formula (VII):

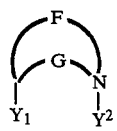

(VII)

where F is one and G is the other of —$(CH_2)_p$— and —$CH_2$— or groups convertible thereto, $Y^1$ is CN or $COL_1$ and $Y^2$ is —$(CH_2)_2W$ where W is CN or $COL_1$ and $L_1$ is a leaving group, and thereafter, or as necessary and in any appropriate order, reducing the carbonyl group in the cyclisation product to hydroxy and dehydrating the resulting alcohol, converting W to COL, $COR_3'$ or $CH_2R_3'$ and converting F and G to —$(CH_2)_p$— and —$CH_2$— as appropriate.

Examples of leaving groups $L_1$ include $C_{1-4}$ alkoxy such as ethoxy.

In the cyclisation process, where $Y^1$ and $Y^2$ both contain carboxy ester groups, the cyclisation is a Dieckmann reaction which is catalysed by a base such as potassium t-butoxide at elevated temperature in a solvent such as toluene and the product is a β-keto ester.

In the cyclisation process, where $Y^1$ and $Y^2$ both contain cyano groups the cyclisation is a Thorpe reaction which is catalysed by a base such as potassium t-butoxide at elevated temperature in a solvent such as toluene and the product, after acid work up, is a β-keto nitrile.

The β-keto ester or nitrile cyclisation product may be reduced by conventional procedures with an alkali metal borohydride such as sodium borohydride in a lower alcohol such as ethanol, to yield the 4-hydroxy compound usually as a mixture of axial and equatorial alcohols. The mixture may be dehydrated under conventional conditions for the formation of an unsaturated system, such as under strongly acidic conditions e.g. with concentrated sulphuric acid and glacial acetic acid, at elevated temperature such as the boiling point of the solvent, the acid reagent optionally acting as the solvent. More preferably the dehydration may be carried out by prior conversion to the mesylate. The axial and equatorial alcohols may be separated by conventional chromatography, and converted into the mesylates under standard conditions, such as methane sulphonyl chloride in the presence of dry pyridine which may function as the solvent. Under these conditions the axial alcohol undergoes dehydration in situ. The mesylate of the equatorial alcohol can be converted into an axial ester derivative, such as the acetate, with sodium acetate in a suitable solvent such as N,N-dimethylformamide, at elevated temperature. The intermediate is not isolated and undergoes elimination to give the required product. Alternatively the mixture of axial and equatorial alcohols may be subjected sequentially to the conditions required for the dehydration of each isomer. It will be appreciated that the reduction and dehydration steps may be carried out before or after the conversion of W to the —$C(R_3)$=$NR_2$ group.

The 4-keto and 4-hydroxy azabicycloalkane moieties are therefore examples of $R_1'$ convertible to $R_1$.

The conversion of W to COL, $COR_3'$ or $CH_2R_3'$ may be carried out conventionally.

A carboxy group may be obtained by conventional de-esterification of a W alkoxycarbonyl or cyano group. A carboxy group may be treated with thionyl chloride at elevated temperature to give the chlorocarbonyl group, COCl or with thionyl bromide to give the bromocarbonyl group, COBr.

An $R_3'CO$— group where $R_3'$ is $C_{1-4}$ alkyl may be obtained from a W cyano group by treatment with the appropriate alkyl lithium in ether at depressed temperature, or by treatment of a LiOOC group with an alkyl lithium, the LiOOC group being obtained by hydrolysis of a W alkoxycarbonyl group with lithium hydroxide in water Alternatively, an $R_3'CO$— group where $R_3'$ is $C_{1-4}$ alkyl may be obtained by reaction of a chlorocarbonyl group with N,O-dimethylhydroxylamine and treatment with an alkyl lithium.

A W cyano or carboxylic acid derivative group such as alkoxycarbonyl or N-methoxy-N-methylamido may be converted to —CHO (i.e. $R_3'CO$— where $R_3'$ is hydrogen) by controlled reduction using a suitable reducing agent such as diisobutylaluminium hydride or lithium aluminium hydride in an inert solvent such as toluene or tetrahydrofuran at low temperature. The formyl group may then be converted to $CH_2CN$ by treatment with p-toluenesulphonylmethyl isocyanide under basic conditions at depressed temperature.

Compounds of formula (IVc) may be prepared as described in EP 0414394, for example by reacting a compound of formula (VIIa):

(VIIa)

with a phosphorus ylide of formula (X) or (XI):

(X)

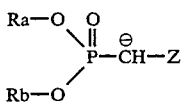 (XI)

in which Ra, Rb and Rc are independently $C_{1-6}$ alkyl, aryl or aralkyl and Z is an electron withdrawing group such as CN or a carboxylic acid, or ester or amide derivative thereof to give a compound of formula (XII):

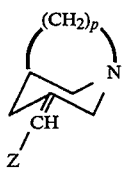 (XII)

in which Z is as defined for formulae (X) and (XI); and thereafter where necessary, converting Z to $R_3'$.

The reaction of a compound of formula (VIIa) with a phosphorus ylide of formula (X) or (XI) which is equivalent to the conversion of a ketone to an olefin is known as a Wittig Reaction and may be carried out under conditions generally used for such reactions. Preferably a compound of formula (VIIa) is reacted with a compound of formula (XI) in which Ra and Rb are each $C_{1-6}$ alkyl, for example ethyl, and Z is cyano.

Where the Z group is a carboxy derivative such as an alkoxycarbonyl group, it may be converted to a cyano group by conventional methods.

However, as stated above, Z is preferably cyano and no conversion is necessary.

Intermediates of formulae (VII) and (VIIa) are known compounds (e.g. as described in Thill et al., J. Org. Chem., 1968, 33, 4376) or may be prepared analogously.

For example, a compound of formula (VIII):

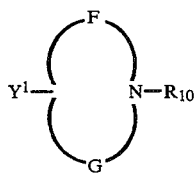 (VIII)

where $Y^1$, F and G are as defined in formula (VII) and $R_{10}$ is hydrogen or an N-protecting group, may be deprotected if necessary by hydrogenation over palladium on carbon, or preferably using Pd/C in the presence of ammonium formate, followed by reaction with ethyl acrylate in ethanol at elevated temperature.

Compounds of formula (VIII) are known compounds or may be prepared by analogous methods to those for preparing known compounds. The compound of formula (VIII) where F is —$(CH_2)_2$—, G is —$CH_2$— and $R_{10}$ is benzyl may be prepared by the cyclisation of di-$C_{1-4}$ alkyl itaconate in the appropriate alkanol with benzylamine at elevated temperature, followed by reduction of the resulting oxo group at the 2-position of the pyrrolidine ring with $BH_3$ in tetrahydrofuran, at ambient to elevated temperature.

Alternatively, and preferably, a dipolar cycloaddition of a $C_{1-4}$ alkyl acrylate with a compound of formula (IX):

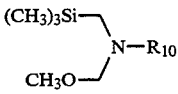 (IX)

in which $R_{10}$ is an N-protecting group in the presence of a catalytic amount of trifluoroacetic acid, yields a compound of formula (VIII) directly.

Compounds of formula (IX) may be prepared conventionally by the reaction of the primary amine $R_{10}NH_2$ successively with chloromethyltrimethylsilane then formaldehyde, methanol and anhydrous potassium carbonate.

Compounds of formula (III) are known compounds or may be prepared by analogous methods to those for preparing known compounds. Certain compounds of formula (III) are commercially available.

The different stereoisomeric forms of compounds of formula (I) may be separated one from the other by the usual methods, for example using chromatographic methods. Enantiomers may be separated using chiral resolving agents or chiral chromatography, or any given isomer may be obtained by stereospecific or asymmetric synthesis.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, or hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg, for example 0.2 to 50 mg and such unit doses may be administered more than once a day, for example two or three times a day, so that the total daily dosage is in the range of about 0.01 to 5 mg/kg and such therapy may extend for a number of weeks or months.

When administered in accordance with the invention no unacceptable toxicological effects are expected for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

DESCRIPTION 1

(±) Ethyl N-benzyl-3-pyrrolidinylcarboxylate (D1)

To a stirred solution of ethyl acrylate (141 g, 1.41 mole) and N-benzyl-N-(methoxymethyl)-N-[(trimethylsilyl)methyl]amine (Compound D17 of EP 0363085, 435 g, containing approximately 75% of D17, 1.4 moles) in dichloromethane (2.5L) at −5° C. was added trifluoroacetic acid (16.1 g, 0.14 mole) in dichloromethane (100 ml) ensuring that the temperature did not rise above 0° C. This mixture was then transferred by cannula to stirred, refluxing dichloromethane (50 ml) over 40 minutes at such a rate as to maintain gentle reflux. The reaction mixture was then refluxed for a further 1h before cooling to room temperature. It was then washed with saturated aqueous potassium carbonate, dried ($Na_2SO_4$), and concentrated in vacuo to a gum which was distilled to afford the title compound (D1) as a clear oil (286 g, 88%) b.p. 120°–150° C. at 4 mmHg.

[1] NMR ($CDCl_3$) δ: 1.23 (3H, t, J=7 Hz), 2.01–2.12 (2H, m), 2.34–2.75 (3H, m), 2.83–3.07 (2H, m), 3.59 (2H, s), 4.10 (2H, q, J=7 Hz ), 7.16–7.33 (5H, m).

DESCRIPTION 2

(±) Ethyl N-(2-ethoxycarbonylethyl)-3-pyrrolidinylcarboxylate (D2)

A solution of (±) ethyl N-benzyl-3-pyrrolidinyl carboxylate (D1) (100 g, 0.43 mole) in ethanol (800 ml) was treated with ammonium formate (135.32 g, 2.15 mole) and 10% Pd on carbon (25 g) then heated at 70° C. for 2h. After 1h a further addition of 10% Pd on carbon (10 g) was made. The reaction mixture was filtered through celite and the filtrate concentrated in vacuo. The residue was partitioned between chloroform and saturated aqueous potassium carbonate solution. The organic phase was separated, dried ($Na_2SO_4$), and concentrated in vacuo. The residue was dissolved in ethanol (500 ml), treated with ethyl acrylate (51.56 g, 0.52 mole) then heated under reflux for 1h. The reaction mixture was concentrated in vacuo, treated with saturated aqueous potassium carbonate, then extracted into chloroform. The combined organic extracts were dried ($Na_2SO_4$), concentrated in vacuo and the residue distilled to afford the title compound (D2) as an oil (60.53 g, 58%), b.p. 135°–145° C. at 4 mmHg.

$^1$H NMR ($CDCl_3$) δ: 1.28 (6H, t, J=7 Hz), 2.03–2.14 (2H, m), 2.47–2.57 (3H, m), 2.61–2.86 (4H, m), 2.87–3.12 (2H, m), 4.15 (4H, q, J=7 Hz).

DESCRIPTION 3

(±) exo-Ethyl-4-oxo-1-azabicyclo[3.2.1]oct-3-yl-carboxylate (D3)

A solution of (±) ethyl N-(2-ethoxycarbonylethyl)-3-pyrrolidinylcarboxylate (D2) (5.77 g, 25.2 mmole) in dry toluene (10 ml) was added dropwise over 1h to a solution of potassium t-butoxide (7.57 g, 55.4 mmoles) in dry toluene (50 ml) at reflux, under nitrogen. After a further 2h at reflux, the reaction mixture was cooled to −5° C. and then quenched by the addition of acetic acid (3.33 ml, 55.4 mmole) keeping the temperature below 0° C. The mixture was filtered, and the filtrate concentrated in vacuo to afford the title compound (D3) as a white solid (2.6 g, 47%) which was used without further purification.

DESCRIPTION 4 AND 5 cis- and trans-exo-Ethyl 4-hydroxy-1-azabicyclo[3.2.1]-oct-3-ylcarboxylate (D4 and D5)

A solution of (±) exo-ethyl-4-oxo-1-azabicyclo[3.2.1]oct-3-ylcarboxylate (D3) (17.71 g, 90 mmole) in dry ethanol (100 ml) was cooled in ice under nitrogen and treated with sodium borohydride (1.7 g, 45 mmole) portionwise over 15 min. The reaction mixture was allowed to warm up to room temperature over 1h. It was then concentrated in vacuo, treated with saturated aqueous potassium carbonate (20 ml) and extracted into chloroform (3×15 ml). The extracts were dried (Na$_2$SO$_4$) then concentrated in vacuo and the residue chromatographed on basic alumina in a gradient of 0–3% methanol in chloroform to afford, in order of elution, the cis isomer (D4) as a clear oil (4.73 g, 26%) and the isomer (D5) as an off-white solid (3.81, 21%).

D4

$^1$H NMR (CDCl$_3$) δ: 1.26 (3H, t, J=7 Hz), 1.57–1.73 (1H, m), 1.85–2.01 (1H, m), 2.27–2.53 (2H, m), 2.59–2.82 (4H, m), 2.87–3.09 (2H, m), 3.97–4.05 (1H, m), 4.16 (2H, q, J=7 Hz).

$^{13}$C NMR (CDCl$_3$) δ: 14.54, 25.48, 40.70, 46.01, 51.95, 55.87, 58.66, 61.25, 71.68, 174.20

D5

$^1$H NMR (CDCl$_3$) δ: 1.26 (3H, t, J=7 Hz), 1.45–1.60 (1H, m), 1.72–1.86 (1H, m), 2.28–2.41 (2H, m), 2.61–2.71 (1H, m), 2.78–3.02 (3H, m), 3.09–3.18 (1H, m), 3.37–3.45 (1H, m), 4.06–4.20 (3H, m)

$^{13}$C NMR (CDCl$_3$) δ: 14.19, 27.72, 39.81, 39.84, 50.29, 52.96, 53.32, 60.91, 68.98, 174.31

DESCRIPTION 6

(±) Ethyl 1-azabicyclo[3.2.1]oct-3-en-3-ylcarboylate (D6)

Method (a)

A solution of (±) cis-exo-ethyl 4-hydroxy-1-azabicyclo[3.2.1]oct-3-ylcarboxylate (D4), (2 g, 10.1 mmole) in dry pyridine (10 ml) at 0° C. was treated dropwise with methanesulphonyl chloride (3.45 g, 30.2 mmole) over fifteen minutes. The reaction mixture was allowed to warm to room temperature over 3h, concentrated in vacuo, then treated with saturated aqueous potassium carbonate (100 ml), and extracted into chloroform (3×100 ml). The combined organic extracts were dried (Na$_2$SO$_4$) and evaporated to give a residue which was chromatographed on neutral alumina in a gradient of 0–2% methanol in chloroform to afford the title compound (D6) as a gum (1 g, 53%).

$^1$H NMR (CDCl$_3$) δ: 1.26 (3H, t, J=7 Hz), 1.80–2.12 (2H, m), 2.57–3.01 (4H, m), 3.06–3.22 (1H, m), 3.35 (1H, d, J=17 Hz), 3.93 (1H, d, J=17 Hz), 4.16 (2H, q, J=7 Hz), 7.19–7.28 (1H, m).

$^{13}$C NMR (CDCl$_3$) δ: 14.25, 33.60, 36.53, 54.52, 55.85, 58.32, 60.25, 126.96, 145.60, 166.35

Method (b)

A solution of (±) trans-exo-ethyl 4-hydroxy-1-azabicyclo[3.2.1]oct-3-ylcarboxylate (D5), (3.9 g, 0.0196 mole) in dry pyridine (50 ml) under nitrogen was treated dropwise with methanesulphonyl chloride (3.8 ml, 0.049 mole) over a period of 0.75h with ice cooling. The mixture was stirred at room temperature for 3h, and then concentrated in vacuo. After co-distillation with dry toluene to remove volatiles, the residue was dried further under high vacuum. The resulting gum was dissolved in dry N,N-dimethylformamide (100 ml), treated with anhydrous sodium acetate (8.2 g, 0.1 mole) and heated to 100° C. over a period of 1h. The reaction was maintained at this temperature for a further 0.75h, and then concentrated in vacuo. After co-distillation with toluene, the residue was treated with a saturated solution of potassium carbonate (25 ml) and extracted into chloroform (4×25 ml). The combined organic extracts were dried (Na$_2$SO$_4$) and concentrated in vacuo to give a crude oil. Purification on silica gel in a gradient of 2–6% methanol in chloroform afforded the title compound (D6) (1.9 g, 54%).

Method (c)

A 3:1 mixture of the cis and trans isomers (D4) and (D5) (9.89 g, 0.050 mole) subjected to the reaction conditions described in Method (b), gave the title compound (D6) (6.23 g, 71%).

DESCRIPTION 7

(±) 1-Azabicyclo[3.2.1]oct-3-en-3-yl-N-methoxycarboxamide (D7)

A solution of (±) ethyl 1-azabicyclo[3.2.1]-oct-3-en-3-ylcarboxylate (D6) (0.52 g, 2.9 mmole) in ethanol (6 ml) was treated with 85% potassium hydroxide (0.38 g, 5.7 mmole) then heated under reflux for 9h. The reaction mixture was concentrated in vacuo, treated with 5N hydrochloric acid (1.72 ml, 8.6 mole) then concentrated in vacuo and co-distilled with toluene to remove the last traces of water. The residue was treated with thionyl chloride (10 ml), heated at reflux under nitrogen for 25 minutes then concentrated in vacuo and co-distilled with toluene to afford the crude acid chloride. A solution of this material in a mixture of dry acetonitrile (12 ml) and dry chloroform (10 ml), under nitrogen, was treated with methoxyamine hydrochloride (0.48 g, 5.8 mmole) then cooled to −30° C. and treated in a single rapid addition with pyridine (1.09 g, 29 mmole) in acetonitrile (2 ml). The reaction mixture was allowed to warm to room temperature and stirred at room temperature overnight. It was then treated with saturated aqueous potassium carbonate (25 ml), the organic phase was separated, and the aqueous phase extracted with chloroform (8×25 ml). The combined organic extracts were dried (Na$_2$SO$_4$), concentrated in vacuo and the residue chromatographed on neutral alumina in a gradient of 0–10% methanol in chloroform to afford the title compound (D7) as a brown gum (0.17 g, 34%).

$^1$H NMR (CDCl$_3$) δ: 1.82–2.12 (2H, m), 2.57–3.02 (4H, m), 3.11–3.26 (1H, m), 3.37 (1H, d, J=17 Hz), 3.68 (3H, s), 3.94 (1H, d, J=17 Hz), 6.84 (1H, d, J=7 Hz).

DESCRIPTION 8

(±) 1-Azabicyclo[3.2.1]oct-3-en-3-yl-N-methoxy-N-methylcarboxamide (D8)

A solution of (±)ethyl 1-azabicyclo[3.2.1]oct-3-en-3-yl carboxylate (D6) (1.9 g, 10.5 mmole) in 5M hydrochloric acid (25 ml) was heated at 100° C. for 7h. The reaction was concentrated in vacuo and dried by co-distillation with toluene. The resulting brown solid (2.0 g) was suspended in thionyl chloride (20 ml) and heated under reflux until all the acid had dissolved (approx. 10 minutes). After concentrating the reaction in vacuo, residual traces of volatile material were removed by co-distillation with toluene, and the residue was finally dried under high vacuum. A suspension of the acid chloride in absolute chloroform (50 ml) was treated with N,O-dimethylhydroxylamine hydrochloride (1.13 g, 11.5 mmole) and cooled in an ice-salt bath. Pyridine (4.2 ml, 5.3 mmole) was added dropwise with good stirring over a period of 1h. The reaction was allowed to warm to room temperature and stirred overnight. After cooling in an ice bath, the reaction was quenched with a saturated aqueous solution of potassium carbonate (25 ml). The aqueous layer was extracted with chloroform (3×25 ml), and the combined organic extracts were dried ($Na_2SO_4$) and concentrated in vacuo to give an oil which was extracted into ether, and then distilled on a kugelröhr (175° C./0.2 mmHg) to afford the title compound (D8) as a pale yellow oil (1.1 g, 54%) which solidified on cooling.

$^1$H NMR ($CDCl_3$) δ: 1.9 (1H, m), 2.1 (1H, m), 2.55 (1H, m), 2.68 (1H, m), 2.9 (1H, m), 3.05 (1H, m), 3.15 (1H, m), 3.20 (3H, s), 3.32 (1H, d, J=17.5 Hz), 3.64 (3H, s), 4.02 (1H, d, J=17.5 Hz), 6.64 (1H, d, J=7 Hz).

DESCRIPTION 9

(±)1-Azabicyclo[3.2.1]oct-3-en-3-ylcarboxaldehyde (D9)

A solution of (±)1-azabicyclo[3.2.1]oct-3-en-3-yl-N-methoxy-N-methylcarboxamide (D8) (0.25 g, 1.28 mmol) in dry tetrahydrofuran (10 ml) was cooled to −70° C. under an atmosphere of nitrogen then treated with 1.5M diisobutylaluminium hydride in toluene (1.1 ml, 1.66 mmole) over 5 minutes. The reaction was allowed to warm up to 0° C. over 1h, then it was cooled to −60° C. and poured into vigorously stirred 5N hydrochloric acid (25 ml) which had been cooled to 0° C. The tetrahydrofuran was removed in vacuo, the aqueous solution was saturated with potassium carbonate and Rochelle salt, then extracted into chloroform (3×30 ml). The combined organic extracts were dried ($Na_2SO_4$), concentrated in vacuo and the residue distilled to afford the title compound (D9) as a clear oil (128 mg, 73%), b.p. 160° C./1 mmHg (kugelröhr apparatus).

$^1$H NMR ($CDCl_3$) δ: 1.89–2.15 (2H, m), 2.67–3.98 (4H, m), 3.09–3.20 (1H, m), 3.32 (1H, d, J=17 Hz), 3.87 (1H, d, J=17 Hz), 7.11–7.19 (1H, m), 9.33 (1H, s).

$^{13}$C NMR ($CDCl_3$) δ: 34.45, 36.62, 54.56, 56.12, 56.26, 137.34, 155.86, 193.12.

DESCRIPTION 10

(±)3-Acetyl-1-azabicyclo[3.2.1]oct-3-ene (D10)

A solution of (±)1-azabicyclo[3.2.1]oct-3-en-3-yl-N-methoxy-N-methylcarboxamide (D8) (0.40 g, 2.0 mmole) in dry tetrahydrofuran (20 ml) was cooled to −70° C., under a nitrogen atmosphere, and treated dropwise over 15 minutes with methyllithium (1.47 ml of a 1.5 m solution in diethyl ether as the complex with lithium bromide, 2.2 mmole). The temperature was maintained at −70° C. for 30 minutes, and then allowed to warm to 0° C. over 1.75h. The reaction was cooled to −20° C. and poured into a 1M solution of orthophosphoric acid (20 ml) cooled below 0° C. The organic layer was separated, and the aqueous phase was saturated with potassium carbonate, and extracted exhaustively with chloroform. The combined organic extracts were dried ($Na_2SO_4$) and concentrated in vacuo to give a pale yellow oil (0.33 g) which was distilled in a kugelröhr at 150° C./0.1 mmHg to give the title compound (D10) as a colourless liquid (0.28 g, 93%).

$^1$H NMR ($CDCl_3$) δ: 1.9–2.23 (2H, m), 2.2 (3H, s), 2.6–3.2 (5H, m), 3.35 (1H, d, J=18 Hz), 3.88 (1H, d, J=18 Hz), 7.18 (1H, d, J=7 Hz).

DESCRIPTION 11

(±) 3-Cyanomethylene-1-azabicyclo[3.2.1]octane (D11).

Diethyl cyanomethylphosphonate (5.67 g, 0.032 mole) in THF (75 ml) was added over 10 minutes to a stirred solution of potassium tert-butoxide (3.60 g, 0.032 mole) in THF (75 ml) at 0° C. The reaction mixture was then cooled to −20° C. before dropwise addition of 1-azabicyclo[3.2.1]octan-3-one* (3.64 g, 0.029 mole) in THF (50 ml) over 15 minutes. The mixture was allowed to warm to room temperature, stirred for 1h, and then poured into 20% aqueous potassium carbonate (150 ml) and extracted with ethyl acetate (3×200 ml). The combined organic extracts were dried ($Na_2SO_4$) and evaporated to give the title compound (D11) as a 6:5 mixture of E and Z isomers (3.88 g, 90%). The isomers could be separated chromatographically on silica using 3% methanol/chloroform as eluant to give in order of elution the Z-isomer and the E-isomer as oils.

Z-isomer
$^1$H NMR ($CDCl_3$) δ: 1.59 (1H, m), 1.77 (1H, m), 2.30 (1H, m), 2.48–3.06 (6H, m), 3.50 (1H, d, J=15 Hz), 3.81 (1H, d, J=15 Hz), 5.16 (1H, d).

$^{13}$C NMR ($CDCl_3$) δ: 29.97, 36.12, 41.71, 52.39, 59.78, 59.96, 96.47, 115.78, 165.00.

E-isomer
$^1$H NMR ($CDCl_3$) δ: 1.61 (1H, m), 1.28 (1H, m), 2.48–2.60 (2H, m), 2.68–2.94 (4H, m), 3.03 (1H, d, J=11 Hz), 3.27 (1H, d, J=15 Hz), 3.59 (1H, d, J=15 Hz), 5.22 (1H, s).

$^{13}$C NMR ($CDCl_3$) δ: 30.05, 35.88, 39.16, 52.24, 59.76, 62.44, 96.48, 115.94, 164.79.

* D. P. Thill and H. S. Aaron, J. Org. Chem., 1968, 33, 4376.

EXAMPLE 1

(±) 1-Azabicyclo[3.2.1]oct-3-en-3-yl-N-methoxycarboximidoyl bromide (E1)

A solution of (±) 1-Azabicyclo[3.2.1]oct-3-en-3-yl-N-methoxycarboxamide (D7) (690 mg, 3.79 mmole) in a mixture of dry ether (45 ml) and methanol (5 ml) was treated with excess hydrogen bromide (1 g) while cooled in ice. The solution was concentrated in vacuo then codistilled with acetonitrile to remove the last traces of methanol. A solution of the residue in dry acetonitrile (100 ml) was treated with carbon tetrabromide (1.38 g, 4.17 mmole) then heated to reflux under nitrogen. It was then treated with triphenylphosphine (1.09 g, 4.17 mmole) and heated under reflux for 5h. Further additions of carbon tetrabromide (1.38 g, 4.17 mmole) and triphenylphosphine (1.09 g, 4.17 mmole) were made over this period. The reaction mixture was concentrated in vacuo, treated with saturated aqueous potassium carbonate (20 ml) then extracted into chloroform (25 ml×3). The combined organic extracts were dried ($Na_2SO_4$) and evaporated to give a residue which was chromatographed on silica in a gradient of 0–7% methanol in chloroform to afford the title compound (E1) as an off-white solid (240 mg, 26%).

$^1$H NMR ($CDCl_3$) δ: 1.76–2.03 (3H, m), 3.58–2.66 (2H, m), 2.69–2.81 (1H, m) 2.86–2.95 (1H, m), 3.07–3.19 (1H, m) 3.38 (1H, d, J=17 Hz), 3.92 (1H, d, J=17 Hz), 3.93 (3H, s), 6.79 (1, d, J=7 Hz).

EXAMPLE 2

(±)
1-Azabicyclo[3.2.1]oct-3-en-3-yl-N-methoxycarboximidoyl chloride oxalate salt (E2)

A refluxing solution of (±) 1-azabicyclo[3.2.1]oct-3-en-3-yl-N-methoxycarboxamide (D7) (80 mg, 0.43 mmole) and carbon tetrachloride (125 mg, 0.82 mmole) in dry acetonitrile (15 ml), under nitrogen, was treated with triphenylphosphine (121 mg, 0.45 mmole) then heated under reflux for 7 min. The reaction mixture was concentrated in vacuo and the residue chromatographed on silica in a gradient of 0-4% methanol in chloroform to afford the imidoyl chloride as a white solid (34 mg, 39%) which was converted to the oxalate salt (E2) m.p. 172° C. (decomp.) (from methanol-ether).

$^1$H NMR (d$_6$-DMSO) δ: 2.01-2.27 (2H, m), 2.98-3.41 (4H, m), 3.48-3.67 (1H, m), 3.89 (1H, d, J=17 Hz), 3.95 (3H, s), 4.26 (1H, d, J=17 Hz), 6.96 (1H, d, J=7 Hz).

$^{13}$C NMR (d$_6$-DMSO) δ: 32.87, 33.14, 52.49, 54.18, 55.18, 63.15, 123.75, 134.49, 137.98.

Analysis: C$_{11}$H$_{15}$N$_2$O$_5$Cl requires C: 45.45; H: 5.11; N: 9.64 found C: 45.54; H: 5.11; N: 9.33

EXAMPLE 3

(±)
1-Azabicyclo[3.2.1]oct-3-en-3-yl-N-methoxcarboximidoyl fluoride oxalate salt (E3)

Method (i) (reaction variant (c))

(±) 1-Azabicyclo[3.2.1]oct-3-en-3-yl-N-methoxycarboxamide (D7) (80 mg, 0.44 mmole) was converted to the hydrofluoride salt by the addition of hydrogen fluoride-pyridine (Aldrich). The salt was dissolved in refluxing acetonitrile (10 ml), diethylaminosulphur- trifluoride (DAST) (74 mg, 0.46 mmole) in acetonitrile (1 ml) was added in a single portion then the reaction mixture was heated under reflux for 30 seconds. It was then concentrated in vacuo, treated with saturated aqueous potassium carbonate (50 ml) and extracted into chloroform (3×75 ml). The combined organic extracted were dried (Na$_2$SO$_4$), concentrated in vacuo and the residue chromatographed on silica in a gradient of 0-4% methanol in chloroform. This afforded the imidoyl fluoride as a white solid (12 mg, 15%).

Method (ii) (reaction variant (b))

A solution of (±) 1-Azabicyclo[3.2.1]oct-3-en-3-yl-N-methoxycarboximidoyl bromide (E1, 0.1 g, 0.4 mmole) in dry N,N-dimethylformamide (7 ml) was treated with cesium fluoride supported on calcium fluoride (4 g)* then heated at 140° C. under nitrogen for 4 days. The reaction mixture was filtered, the solid washed with more N,N-dimethylformamide and the filtrate concentrated in vacuo. It was then treated with saturated aqueous potassium carbonate (50 ml) then extracted into chloroform (3×75 ml). The combined organic extracts were dried (Na$_2$SO$_4$) and then concentrated in vacuo and the residue chromatographed on silica in a gradient of 0-3% methanol in chloroform to afford the imidoyl fluoride contaminated with about 25% (E1) (10 mg, 13%). This was combined with the material produced using method (a) and converted to the oxalate salt which was recrystallised from methanol/ether to give the title compound (E3) which contained about 9% (E1).

$^1$H NMR (d$_6$-DMSO) δ: 2.12-2.21 (2H, m), 3.08-3.73 (5H, m), 3.75 (1H, d, J=16 Hz), 3.90 (3H, s), 4.16 (1H, d, J=16 Hz), 6.92 (1H, d, J=7 Hz).

$^{13}$C NMR (d$_6$-DMSO) δ: 32.74, 32.98, 52.67, 53.62, 54.25, 62.97, 118.12 (d, $^2J_{CF}$=29 Hz), 136.50, 147.40 (d, $^1J_{CF}$=320 Hz).

MS Calculated mass for C$_9$H$_{13}$ON$_2$F=184.1014 Observed mass=184.1011

*J. Chem. Soc., Chem. Commun., 791 (1986).

Method (iii) (reaction variant (c))

Diethylaminosulphurtrifluoride (DAST) (1.58 g, 9.80 mmol) in acetonitrile (5 ml) was added in a single portion to (±)1-azabicyclo[3.2.1]oct-3-en-3-yl-N-methoxycarboxamide (D7) (1.7 g, 9.34 mmol) in acetonitrile (80 ml) at reflux. The reaction mixture was then immediately poured into saturated aqueous potassium carbonate (75 ml) and extracted with chloroform (3×100 ml). The combined organic extracts were dried (Na$_2$SO$_4$) and evaporated to a gum which was chromatographed on silica using 2% methanol/chloroform to give the imidoyl fluoride (0.39 g, 23%) as a crystallising oil. A portion of this material was converted to the oxalate salt to give the title compound (E3) as a white crystalline solid mpt 153°-155° C. (decomp.).

Analysis C$_9$H$_{13}$N$_2$OF.C$_2$H$_2$O$_4$ requires C:48.18; H:5.51; N;10.21 found C:48.10; H:5.53; N:10.05.

EXAMPLE 4

(±)
syn-1-Azabicyclo[3.2.1]oct-3-en-3-ylcarboxaldehyde-O-methyloxime hydrochloride salt (E4)

A solution of (±)1-azabicyclo[3.2.1]oct-3-en-3-ylcarboxaldehyde (D9) (108 mg, 0.79 mmole) in dry methanol (7 ml) was treated with methoxylamine hydrochloride (73 mg, 0.87 mmole) and stirred for 17h at room temperature, under nitrogen. The reaction mixture was concentrated in vacuo, treated with saturated aqueous potassium carbonate (25 ml) then extracted into chloroform (3×30 ml). The combined organic extracts were dried (Na$_2$SO$_4$), concentrated in vacuo and the residue was chromatographed on silica eluting with 5% methanol in chloroform. This afforded the aldoxime ether (76 mg, 58%) which was converted into the hydrochloride salt and recrystallised from methanol/diethyl ether to afford the title compound (E4) as a white crystalline solid m.p. 214° C. (decomp.).

$^1$H NMR (d$_6$-DMSO) δ: 2.10-2.35 (2H, m), 3.25-3.49 (4H, m), 3.61-3.77 (1H, m), 3.89 (3H, s), 3.91 (1H, d, J=17 Hz), 4.30 (1H, d, J=17 Hz), 6.67-6.74 (1H, m), 8.94 (1H, s).

$^{13}$C NMR (d$_6$-DMSO) δ: 32.97, 33.41, 52.72, 54.34, 54.66, 61.94, 124.71, 138.48, 148.25.

EXAMPLE 5

(±)trans
3-Acetyl-1-azabicyclo[3.2.1]oct-3-ene-O-methyloxime hydrochloride salt (E5)

A solution of (±)3-acetyl-1-azabicyclo[3.2.1]oct-3-ene (D10) (0.27 g, 1.79 mmole) in methanol (15 ml) was treated with methoxylamine hydrochloride (0.16 g, 1.96 mmole). After stirring overnight at room temperature, the reaction was concentrated in vacuo and treated with a saturated aqueous solution of potassium carbonate (10 ml). The mixture was extracted with chloroform (4×10 ml) and the organic layers were dried (Na$_2$SO$_4$) and concentrated to give a crude oil which was purified on a silica gel column using a graded eluant of 5–15% methanol in chloroform. Pooling of pure fractions containing the major faster running component afforded the required oxime ether as an oil (0.19 g, 59%) which was converted into the title hydrochloride salt (E5) m.p. 241°–243° C. (from methanol-ether).

$^1$H NMR (d$_6$-DMSO) δ: 1.95 (3H, s), 2.1–2.4 (2H, m), 3.1–3.8 (6H, m), 4.0 (3H, s), 4.28 (1H, d, J=16 Hz), 6.78 (1H, d, J=7 Hz).

$^{13}$C NMR (d$_6$-DMSO) δ: 9.79, 32.65, 32.98, 52.25, 54.04, 54.83, 61.74, 126.17, 133.38, 152.58.

Analysis: $C_{11}H_{17}N_2OCl$ requires C: 55.42; H: 7.91; N:12.93 found C: 55.05; H:7.90; N: 12.73.

EXAMPLE 6

(±)-α-(Methoxyimino)-α-(1-azabicyclo[3.2.1]oct-3-en-3-yl)acetonitrile oxalate salt (E6)

Potassium tert-butoxide (0.807 g, 7.19 mmol) was added portionwise to a solution of (±)3-cyanomethylene-1-azabicyclo[3.2.1]octane (D11) (0.967 g, 6.53 mmol) in THF (40 ml) at −70° C. The resulting solution was stirred for 0.5h at −60° C., then tert-butyl nitrite (0.87 ml of approximately 90% purity, 6.58 mmol) was added dropwise. The reaction mixture was allowed to warm to room temperature and stirred for 1.5h. Methyl p-toluenesulphonate (1.215 g, 6.53 mmol) in THF (10 ml) was added dropwise and the resulting mixture was stirred at room temperature overnight, then poured into saturated aqueous potassium carbonate (75 ml) and extracted with ethyl acetate (3×100 ml). The combined organic extracts were dried (Na$_2$SO$_4$) and evaporated to a gum which was subjected to column chromatography on silica in a gradient of 1–5% methanol in chloroform to afford in order of elution (±)-α-(methoxyimino)-α-(1-azabicyclo[3.2.1]oct-2-en-3-yl)acetonitrile (0.683 g, 55%) as a crystallising oil and (±)-α-(methoxyimino)-α-(1-azabicyclo[3.2.1]oct-3-en-3-yl)acetonitrile (0.194 g, 16%) as an oil. The latter compound was converted to the oxalate salt and recrystallised from acetone/methanol to give the title compound (E6) as a white crystalline solid m.p. 196°–198° C.

$^1$H NMR (d$_6$-DMSO) δ: 2.14 (2H, m), 3 07–3 36 (4H, m), 3.55 (1H, m) 3.85 (1H, d, J=15 Hz), 4.06 (3H, s), 4.22 (1H, d, J=15 Hz), 6.86 (1H, d, J=5 Hz).

$^{13}$C NMR (d$_6$-DMSO) δ: 32.90, 33.37, 52.56, 54.16, 54.32, 64.41, 108.06, 123.23, 130.24, 139.39.

Analysis $C_{10}H_{13}N_3O \cdot C_2H_2O_4$ requires C:51.24; H:5.38; N:14.94 found C:51.24; H:5.38; N:14.88.

| Compound | R$_2$ | R$_3$ | P |
|---|---|---|---|
| E1 | CH$_3$O | Br | 2 |
| E2 | CH$_3$O | Cl | 2 |
| E3 | CH$_3$O | F | 2 |
| E4 | CH$_3$O | H | 2 |
| E5 | CH$_3$O | CH$_3$ | 2 |
| E6 | CH$_3$O | CN | 2 |

BIOLOGICAL ACTIVITY

Radio Ligand Binding

Cerebral cortex from Hooded Lister rats (Olac, UK) is homogenised in 2.5 vols ice-cold 50 mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1 ml aliquots at −20° C.

Incubations (total volume 2 ml) are prepared using the above buffer with the addition of 2 mM magnesium chloride in the 3H-Oxotremorine-M (3H-OXO-M) experiments. For 3H-Quinuclidinyl Benzilate (3H-QNB), 1 ml of stored membranes is diluted to 30 ml and 0.1 ml mixed with test compound and 0.27 nM (c. 25,000 cpm) 3H-QNB (Amersham International). For 3H-OXO-M, 1 ml of membranes is diluted to 6 ml and 0.1 ml mixed with test compound and 2 nM (c. 250,000 cpm) 3H-OXO-M (New England Nuclear).

Non-specific binding of 3H-QNB is defined using 1 μM Atropine sulphate (2 μM Atropine) and of 3H-OXO-M using 10 μM Oxotremorine. Non-specific binding values typically are 5% and 25% of total binding, respectively. Incubations are carried out at 37° C. for 30 min and the samples filtered using Whatman GF/B filters. (In the 3H-OXO-M experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluor 30 (Packard) as scintillant.

This test provides an indication of the muscarinic binding activity of the test compound. The results are obtained as IC$_{50}$ values (i.e. the concentration which inhibits binding of the ligand by 50%) for the displacement of the muscarinic agonist 3H-OXO-M and the muscarinic antagonist 3H-QNB. The ratio IC$_{50}$(3H-QNB)/IC$_{50}$(3H-OXO-M) gives an indication of the agonist character of the compound. Agonists typically exhibit a large ratio; antagonists typically exhibit a ratio near to unity. The results are shown in Table 1.

TABLE 1

| Compound | [3H]-OXO-M IC$_{50}$ (nM) | [3H]-QNB IC$_{50}$ (nM) |
|---|---|---|
| E2 | 100 | 1,100 |
| E3 method (iii) | 26 | 320 |
| E4 | 70 | 1,250 |
| E5 | 175 | 1,450 |
| E6 | 21 | 330 |

We claim:

1. A compound of Formula (I) or a pharmaceutically acceptable salt thereof:

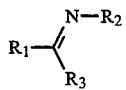
(I)

wherein R$_1$ represents

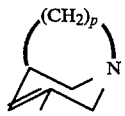

in which p represents 2 or 3;

R$_2$ is a group OR$_4$, where R$_4$ is C$_{1-4}$alkyl, C$_{2-4}$ alkenyl, C$_{2-4}$ alkynyl, a group OCOR$_5$ where R$_5$ is hydrogen or R$_4$, or a group NHR$_6$ or NR$_7$R$_8$ where R$_6$, R$_7$ and R$_8$ are independently C$_{1-2}$alkyl; and R$_3$ is chloro, fluoro, bromo, C$_{1-3}$alkyl substituted by one, two or three halogen atoms, or R$_3$ is —CN, —CH$_2$CN, —OCH$_3$, —CH$_2$SH, —SCH$_3$ and —CH$_2$SCH$_3$.

2. A compound according to claim 1 wherein p is 2.

3. A compound according to claim 1 wherein R$_4$ and R$_5$ in R$_2$ are selected from methyl, ethyl, allyl and propargyl and R$_6$, R$_7$ and R$_8$ in R$_2$ are methyl.

4. A compound according to claim 1 wherein R$_3$ is selected from chloro, fluoro, bromo, CN, —OCH$_3$, and —CH$_2$CN.

5. A compound according to claim 1 selected from the group consisting of:

(±)1-azabicyclo[3.2.1]oct-3-en-3-yl-N-methoxy-carboximidoyl bromide, (±)1-azabicyclo[3.2.1]oct-3-en-3-yl-N-methoxy-carboximidoyl chloride, (±)1-azabicyclo[3.2.1]oct-3-en-3-yl-N-methoxy-carboximidoyl flouride, and (±)-a-(methoxyimino)-a-(1-azabicyclo[3.2.1]oct-3-en-3-yl)acetonitrile.

6. A pharmaceutical composition which comprises an effective amount of a compound according to claim 1 and a pharmaceutically acceptable carder.

7. A method of treatment and/or prophylaxis of dementia in mammals including humans, which comprises administering to the sufferer an effective amount of a compound of formula (I) according to claim 1 or a pharmaceutically acceptable salt thereof.

* * * * *